United States Patent
Akashi et al.

(10) Patent No.: US 7,956,241 B2
(45) Date of Patent: Jun. 7, 2011

(54) PLANT HAVING ENHANCED ROOT ELONGATION AND METHOD FOR PRODUCTION THEREOF

(75) Inventors: Kinya Akashi, Ikoma (JP); Akiho Yokota, Ikoma (JP); Kazuya Yoshimura, Ikoma (JP)

(73) Assignee: National University Corporation Nara Institute of Science and Technology, Nara (JP)

( * ) Notice: Subject to any disclaimer, the term of this patent is extended or adjusted under 35 U.S.C. 154(b) by 37 days.

(21) Appl. No.: 12/224,439

(22) PCT Filed: Mar. 2, 2007

(86) PCT No.: PCT/JP2007/054041
§ 371 (c)(1),
(2), (4) Date: Aug. 27, 2008

(87) PCT Pub. No.: WO2007/100094
PCT Pub. Date: Sep. 7, 2007

(65) Prior Publication Data
US 2009/0055971 A1 Feb. 26, 2009

(30) Foreign Application Priority Data

Mar. 3, 2006 (JP) ................................. 2006-058746

(51) Int. Cl.
*C12N 15/29* (2006.01)
*C12N 15/82* (2006.01)
*A01H 5/00* (2006.01)
(52) U.S. Cl. ........ 800/278; 800/298; 800/290; 536/23.6
(58) Field of Classification Search .................. None
See application file for complete search history.

(56) References Cited

U.S. PATENT DOCUMENTS 6,759,576 B2 * 7/2004 Zhang et al. ................. 800/308
2004/0034888 A1 2/2004 Liu et al.

OTHER PUBLICATIONS

Merriam Webster Online Dictionary. 2008, www.m-w.com/home.html.*
Wang et al (2006, Plant Physiology 140:91-101).*
Bowie et al, Science 247:1306-1310, 1990.*
McConnell et al, Nature 411 (6838):709-713, 2001.*
Grumet et al (2003, NCBI Accession No. CK086037).*
Theisen et al (2002, NCBI Accession No. AF495716).*
Merkle, T. et al., "Phenotype of the fission yeast cell cycle regulatory mutant *pim1-46* is suppressed by a tobacco cDNA encoding a small, Ran-like GTP-binding protein", *The Plant Journal*, (1994), 6(4): 555-565.
Haizel, T. et al., "Characterization of proteins that interact with the GTP-bound form of the regulatory GTPase Ran in *Arabidopsos*", *The Plant Journal*, (1997), 11(1): 93-103.
Ach, R. and Gruissem, W., "A small nuclear GTP-binding protein from tomato suppresses a *Schizosaccharomyces pombe* cell-cycle mutant", *Proc. Natl. Acad. Sci.*, (1994), 91: 5863-5867.
Masuda, A. et al., "Proteome Analysis of Drought Stress Avoidance/Defense Mechanism in the Root of a Wild Watermelon", *The 47th Annual Meeting of the Japanese Society of Plant Physiologists*, (2006), Abstract 2aK03, p. 181. (Translation).
Doerner, P. et al., "Control of root growth and development by cyclin expression", *Nature*, (1996), 380: 520-523.
Wang, X. et al., "Overexpression of *RAN1* in Rice and *Arabidopsis* Alters Primordial Meristem, Mitotic Progress, and Sensitivity to Auxin", *Plant Physiology*, (2006), 140: 91-101.

* cited by examiner

*Primary Examiner* — Stuart F. Baum
(74) *Attorney, Agent, or Firm* — Wenderoth, Lind & Ponack L.L.P.

(57) ABSTRACT

An object of the present invention is mainly to provide, using a genetically engineering technique, a plant with enhanced root elongation; a plant immune to suppression in root elongation ability even under hyperosmotic stress; and a method for enhancing plant root elongation. The subject invention produces a transgenic plant in which a Ran protein derived from a wild watermelon (*Citrullus lanatus*) is expressed, using a genetically engineering technique.

10 Claims, 3 Drawing Sheets

SEQUENCE LISTING

<160> NUMBER OF SEQ ID NOS: 8

<210> SEQ ID NO 1
<211> LENGTH: 666
<212> TYPE: DNA
<213> ORGANISM: Citrullus lanatus

<400> SEQUENCE: 1

```
atggctttgc cggaccagaa gactgttgat tatccgagtt tcaagcttgt tattgttggt      60
gatggtggca ctggaaaaac aacatttgtg aaaagacatc tcacagggga gttcgaaaag     120
aaatacgaac caaccattgg tgtggaggtg cacccattgg acttcttcac taactgtgga     180
aaaattagat tttactgttg ggacactgct gggcaggaga aatttggtgg tttacgtgat     240
ggctactaca tccatgggca atgtgcaatc atcatgtttg atgttactgc cagattgaca     300
tataaaaatg ttccgacgtg gcaccgtgat ctttgcagag tgtgtgagaa tattccaata     360
gttctttgtg gaaacaaggt cgatgtgaaa acaggcagg ttaaggccaa gcaagtcaca     420
ttccacagga agaagaacct acagtactat gaaatatctg caaagagtaa ctacaacttc     480
gaaaaaccat tcctgtactt ggccagaaag ttggctgggg atccaaacat tcatttcgtg     540
gagtctccag ctctggctcc tcctgaagta cacattgatt tggctgccca gcaacagcat     600
gaagctgaat tagcggcagc agcaagtcaa cctcttcccg acgatgacga cgacgcgttc     660
gagtaa                                                                666
```

<210> SEQ ID NO 2
<211> LENGTH: 666
<212> TYPE: DNA
<213> ORGANISM: Citrullus lanatus

<400> SEQUENCE: 2

```
atggcgctac caaatcaggc caccgtagat taccctagct tcaagcttgt aattgtcgga      60
gatggtggaa cagggaagac aacctttgtt aaacgtcatc ttactggaga gttcgagaag     120
aaatatgaac cgacaatcgg agttgaagtt catccactgg acttctttac aaactatgga     180
aagataaggt tttactgctg ggatactgct ggacaggaga agtttggtgg acttagagat     240
ggttactata ttcatgggca atgtgccatt atcatgtttg atgtcactgc tcgtttaaca     300
tacaaaaatg tcccaacatg gcatcgtgat ctctgcaggg tttgtgagaa catacccatc     360
gtattgtgtg gaaacaaggt cgacgtgaaa acagacagg ttaaagcaaa gcaggtcacc     420
ttccacagga agaaaaatct tcagtattac gaaatctctg caaagagtaa ttacaacttt     480
gagaagccct tcttgtacct tgccagaaag cttgctggta tccggagct tcacttcgtt     540
```

```
gaatcacctg ccctggctcc tcctgaagtt caaattgact tggccgcaca agcacagcat    600
gaagcagagt tggcgcaagc tgctgcacaa cctcttcctg atgaagatga cgatgcattt    660
gagtaa                                                                666
```

<210> SEQ ID NO 3
<211> LENGTH: 221
<212> TYPE: PRT
<213> ORGANISM: Citrullus lanatus

<400> SEQUENCE: 3

```
Met Ala Leu Pro Asp Gln Lys Thr Val Asp Tyr Pro Ser Phe Lys Leu
1               5                   10                  15

Val Ile Val Gly Asp Gly Gly Thr Gly Lys Thr Thr Phe Val Lys Arg
            20                  25                  30

His Leu Thr Gly Glu Phe Glu Lys Lys Tyr Glu Pro Thr Ile Gly Val
        35                  40                  45

Glu Val His Pro Leu Asp Phe Phe Thr Asn Cys Gly Lys Ile Arg Phe
    50                  55                  60

Tyr Cys Trp Asp Thr Ala Gly Gln Glu Lys Phe Gly Gly Leu Arg Asp
65                  70                  75                  80

Gly Tyr Tyr Ile His Gly Gln Cys Ala Ile Ile Met Phe Asp Val Thr
                85                  90                  95

Ala Arg Leu Thr Tyr Lys Asn Val Pro Thr Trp His Arg Asp Leu Cys
            100                 105                 110

Arg Val Cys Glu Asn Ile Pro Ile Val Leu Cys Gly Asn Lys Val Asp
        115                 120                 125

Val Lys Asn Arg Gln Val Lys Ala Lys Gln Val Thr Phe His Arg Lys
    130                 135                 140

Lys Asn Leu Gln Tyr Tyr Glu Ile Ser Ala Lys Ser Asn Tyr Asn Phe
145                 150                 155                 160

Glu Lys Pro Phe Leu Tyr Leu Ala Arg Lys Leu Ala Gly Asp Pro Asn
                165                 170                 175

Ile His Phe Val Glu Ser Pro Ala Leu Ala Pro Pro Glu Val His Ile
            180                 185                 190

Asp Leu Ala Ala Gln Gln Gln His Glu Ala Glu Leu Ala Ala Ala Ala
        195                 200                 205

Ser Gln Pro Leu Pro Asp Asp Asp Asp Ala Phe Glu
    210                 215                 220
```

<210> SEQ ID NO 4
<211> LENGTH: 221
<212> TYPE: PRT
<213> ORGANISM: Citrullus lanatus

<400> SEQUENCE: 4

```
Met Ala Leu Pro Asn Gln Ala Thr Val Asp Tyr Pro Ser Phe Lys Leu
1               5                   10                  15

Val Ile Val Gly Asp Gly Gly Thr Gly Lys Thr Thr Phe Val Lys Arg
            20                  25                  30

His Leu Thr Gly Glu Phe Glu Lys Lys Tyr Glu Pro Thr Ile Gly Val
        35                  40                  45

Glu Val His Pro Leu Asp Phe Phe Thr Asn Tyr Gly Lys Ile Arg Phe
    50                  55                  60

Tyr Cys Trp Asp Thr Ala Gly Gln Glu Lys Phe Gly Gly Leu Arg Asp
65                  70                  75                  80

Gly Tyr Tyr Ile His Gly Gln Cys Ala Ile Ile Met Phe Asp Val Thr
```

```
            85                  90                  95
Ala Arg Leu Thr Tyr Lys Asn Val Pro Thr Trp His Arg Asp Leu Cys
                100                 105                 110

Arg Val Cys Glu Asn Ile Pro Ile Val Leu Cys Gly Asn Lys Val Asp
            115                 120                 125

Val Lys Asn Arg Gln Val Lys Ala Lys Gln Val Thr Phe His Arg Lys
    130                 135                 140

Lys Asn Leu Gln Tyr Tyr Glu Ile Ser Ala Lys Ser Asn Tyr Asn Phe
145                 150                 155                 160

Glu Lys Pro Phe Leu Tyr Leu Ala Arg Lys Leu Ala Gly Asn Pro Glu
                165                 170                 175

Leu His Phe Val Glu Ser Pro Ala Leu Ala Pro Pro Glu Val Gln Ile
            180                 185                 190

Asp Leu Ala Ala Gln Ala Gln His Glu Ala Glu Leu Ala Gln Ala Ala
            195                 200                 205

Ala Gln Pro Leu Pro Asp Glu Asp Asp Asp Ala Phe Glu
    210                 215                 220

<210> SEQ ID NO 5
<211> LENGTH: 19
<212> TYPE: DNA
<213> ORGANISM: Citrullus lanatus

<400> SEQUENCE: 5
gataccttcc tctcgcttt                                             19

<210> SEQ ID NO 6
<211> LENGTH: 20
<212> TYPE: DNA
<213> ORGANISM: Citrullus lanatus

<400> SEQUENCE: 6
gcaaagagca tcatcaccac                                            20

<210> SEQ ID NO 7
<211> LENGTH: 28
<212> TYPE: DNA
<213> ORGANISM: Citrullus lanatus

<400> SEQUENCE: 7
aaaaagcagg ctccttttcc aatggctt                                   28

<210> SEQ ID NO 8
<211> LENGTH: 28
<212> TYPE: DNA
<213> ORGANISM: Citrullus lanatus

<400> SEQUENCE: 8
agaaagctgg gttttttact cgaacgcg                                   28
```

PLANT HAVING ENHANCED ROOT ELONGATION AND METHOD FOR PRODUCTION THEREOF

This application is a U.S. national stage of International Application No. PCT/JP2007/054041 filed Mar. 2, 2007.

TECHNICAL FIELD

The present invention relates to a polypeptide that promotes plant root elongation, a polypeptide that inhibits the suppression of elongation in plant roots under hyperosmotic stress, and a polynucleotide encoding thereof. The present invention also relates to a plant having enhanced root elongation, a plant whose root elongation capability is not suppressed even under hyperosmotic stress, and a method of production thereof. Further, the present invention relates to a method for enhancing plant root elongation.

BACKGROUND ART

The earth is now facing serious problems like global warming and desertification. In recent years, rapid increases in the global population, decreases in crop yield due to unusual weather, and the like have raised concerns about a major, worldwide food crisis. Increasing productivity by improving growth of crops and plant growth in tree plantation has been considered one of the possible effective strategies to solve such problems.

Chemical fertilizers, agrichemicals and the like have been developed to improve plant growth, and are conventionally in practical use. However, in consideration of their effects on the plants themselves, and their effects on the human body, the usage amount of chemical fertilizers and agrichemicals must be restricted. Particularly in the harvesting of crops, chemical-free farming has now increased in order to reduce the adverse effects on human body, even at the expense of productivity.

As a technology to improve plant growth without using chemical fertilizers or agrichemicals, some methods for enhancing plant root elongation using genetic engineering have been reported. For example, Non-Patent Document 1 reports that overexpressing a cyclin gene in plants result in enhancing root elongation and growth in the parts above ground.

Ran protein is known as a factor involved in important cellular phenomena in plants, such as nuclear membrane-mediated protein transport, formation of microtubules during mitosis, cell cycle control, and the like. In recent years, the suppression of root elongation (see Non-Patent Document 2) through the introduction of a wheat-derived Ran gene into rice or *Arabidopsis* was reported. Based on this, the introduction of the Ran gene into plants has been thought to adversely affect plant growth.

Furthermore, even though it is well known that plant root in dry soil, hypersaline soil or the like is exposed to hyperosmotic stress and therefore have their elongation suppressed, no means of stably elongating roots under such hyperosmotic stress have been known.

Non-Patent Document 1: Doerner et al., (1996) Nature, 380: 520-523

Non-Patent Document 2: Xin Wang et al., (2006) Plant Physiology, 140: 91-101

DISCLOSURE OF THE INVENTION

Problems to be Solved by the Invention

The present invention was made in view of the above background art, and an object is to provide a technology to improve growth of crops, plant growth in tree plantation and the like. More specifically, major objects of the present invention are to provide, using genetic engineering techniques, a plant having enhanced root elongation; a plant whose root elongation capability is not suppressed even under hyperosmotic stress; a method for enhancing plant root elongation; and the like.

Means for Solving the Problems

The present inventors conducted thorough research to solve the above problems, and discovered that Ran protein of wild watermelon (*Citrullus lanatus*; hereinafter abbreviated as "wild watermelon"), which grows in Africa's Kalahari Desert located in the vicinity of the Republic of Botswana, can promote root elongation, and that plants with an artificial expression of the wild watermelon-derived Ran gene were found to have enhanced root elongation. Such plants demonstrated less suppression of root elongation under hyperosmotic stress compared with the wild type, and excellent growth ability under hyperosmotic stress. The inventors conducted further research based on these findings to improve the technology, and completed the present invention.

Specifically, the present invention provides inventions with the following aspects:

Item 1. A polynucleotide comprising a DNA of (a) or (b) below:

(a) a DNA consisting of a base sequence represented by SEQ ID NO: 1 or 2; or (b) a DNA that hybridizes with a DNA complementary to the DNA consisting of a base sequence represented by SEQ ID NO: 1 or 2 under stringent conditions, and that encodes a protein having an activity of enhancing elongation of plant roots and an activity of inhibiting suppression of plant root elongation under hyperosmotic stress.

Item 2. A polynucleotide encoding a polypeptide of any of (c), (d) or (e) below:

(c) a polypeptide consisting of an amino acid sequence represented by SEQ ID NO: 3 or 4;

(d) a polypeptide that consists of an amino acid sequence represented by SEQ ID NO: 3 or 4 in which one or several amino acids are substituted, deleted, or added, and that has an activity of enhancing elongation of plant roots and an activity of inhibiting suppression of plant root elongation under hyperosmotic stress; or (e) a polypeptide that has homology of not less than 70% with the amino acid sequence represented by SEQ ID NO: 3 or 4, and that has an activity of enhancing elongation of plant roots and an activity of inhibiting suppression of plant root elongation under hyperosmotic stress.

Item 3. A polypeptide of any of (c), (d) or (e) below:

(c) a polypeptide consisting of an amino acid sequence represented by SEQ ID NO: 3 or 4;

(d) a polypeptide that consists of an amino acid sequence represented by SEQ ID NO: 3 or 4 in which one or several amino acids are substituted, deleted, or added, and that has an activity of enhancing elongation of plant roots; or (e) a polypeptide that has homology of not less than 70% with the amino acid sequence represented by SEQ ID NO: 3 or 4, and that has an activity of enhancing elongation of plant roots.

Item 4. A recombinant vector comprising the polynucleotide of Item 1.

Item 5. A transgenic plant transformed with the polynucleotide of Item 1.

Item 6. A method for producing a plant having enhanced root elongation, comprising the step of transforming a plant with the polynucleotide of Item 1.

Item 7. A method for producing a plant immune to suppression of root elongation under hyperosmotic stress, comprising the step of introducing the polynucleotide of Item 1 into a plant cell.

Item 8. A method for enhancing plant root elongation, comprising introducing the polynucleotide of Item 1 into a plant cell.

Item 9. An agent for enhancing plant root elongation, comprising the polynucleotide of Item 1.

Item 10. An agent for enhancing plant root elongation according to Item 9, said polynucleotide is contained in a form of the recombinant vector of Item 4.

Item 11. Use of the polynucleotide of Item 1 to enhance plant root elongation.

Item 12. Use according to Item 11, wherein said polynucleotide is used in a form of the recombinant vector of Item 4.

Item 13. Use of the polynucleotide of Item 1 to produce an agent for enhancing plant root elongation.

Item 14. Use according to Item 13, wherein said polynucleotide is used in a form of the recombinant vector of Item 4.

Item 15. An agent for enhancing plant root elongation, comprising the polypeptide of Item 3.

Item 16. Use of the polypeptide of Item 3 to enhance plant root elongation.

Item 17. Use of the polypeptide of Item 3 to produce an agent to enhance plant root elongation.

Item 18. A method for inhibiting suppression of plant root elongation under hyperosmotic stress, comprising introducing the polynucleotide of Item 1 into a plant.

Item 19. An agent for supporting plant root growth under hyperosmotic stress, comprising the polynucleotide of Item 1.

Item 20. An agent for supporting plant root growth according to Item 19, wherein said polynucleotide is contained in the form of the recombinant vector of Item 4.

Item 21. Use of the polynucleotide of Item 1 to inhibit the suppression of plant root elongation under hyperosmotic stress.

Item 22. Use according to Item 20, wherein said polynucleotide is used in the form of the recombinant vector of Item 4.

Item 23. Use of the polynucleotide of Item 1 to produce an agent for supporting plant root growth under hyperosmotic stress.

Item 24. Use according to Item 23, wherein said polynucleotide is used in the form of the recombinant vector of Item 4.

Item 25. An agent for supporting plant root growth under hyperosmotic stress, comprising the polypeptide of Item 3.

Item 26. Use of the polypeptide of Item 3 to inhibit the suppression of plant root elongation under hyperosmotic stress.

Item 27. Use of the polypeptide of Item 3 to produce an agent for supporting plant root growth.

Item 28. A kit for producing a plant having enhanced root elongation, or a plant immune to suppression of root elongation under hyperosmotic stress, said kit comprising the recombinant vector of claim 4.

Effects of the Invention

The transgenic plant of the present invention has enhanced root elongation, and is therefore capable of growing better under low-water conditions compared with the wild type.

Further, the transgenic plant of the present invention is immune to suppression of root elongation caused by hyperosmotic stress, and the root can vigorously grow even in dry soil or hypersaline soil. Therefore, the transgenic plant of the present invention can be grown even under hyperosmotic conditions.

BRIEF DESCRIPTION OF THE DRAWINGS

FIG. 4 shows the examination results of Experimental Example 2; a graph of primary root lengths in the growth of the recombinant *Arabidopsis* obtained in Example 3 under hyperosmotic stress. In FIG. 4, the "+" shown in the PEG column notes the addition of 5 wt. % polyethylene glycol 6,000, while the "−" in the column notes no addition of polyethylene glycol.

BEST MODE FOR CARRYING OUT THE INVENTION

Wild Watermelon-Derived Ran Gene

The present invention provides a polynucleotide encoding a wild watermelon-derived Ran protein (hereinafter, occasionally abbreviated as "Ran gene of the present invention"). The wild watermelon-derived Ran protein has the effect of enhancing root elongation in plants, unlike Ran proteins derived from wheat and other plants. The wild watermelon-derived Ran protein also has a particular characteristic of inhibiting the suppression of root elongation in plants under hyperosmotic stress.

Specifically, the Ran gene of the present invention is a polynucleotide comprising a DNA of the following (a) or (b):

(a) a DNA consisting of a base sequence represented by SEQ ID NO: 1 or 2;

(b) a DNA that hybridizes with a DNA complementary to the DNA consisting of a base sequence represented by SEQ ID NO: 1 or 2 under stringent conditions, and that encodes a protein having an activity of enhancing elongation of plant roots and an activity of inhibiting suppression of plant root elongation under hyperosmotic stress.

Herein, regarding the DNA of (b) above, stringent conditions imply, for example, hybridization in a 5×SSC solution (composition of a 1-fold SSC solution: 150 mM sodium chloride, 15 mM sodium citrate) at 65° C., and subsequent washing in a 0.1% SDS-containing 0.5×SSC solution at 65° C. Each hybridization process under stringent conditions can be carried out by known methods, such as that described in "Molecular Cloning (Third Edition)" (J. Sambrook & D. W. Russell, Cold Spring Harbor Laboratory Press, 2001), and the like. Typically, the higher the temperature and the lower the salt concentrations, the higher the stringency becomes.

DNA that hybridizes under stringent conditions generally has homology of above a certain level with a base sequence of the DNA used as a probe, in which said homology is, for example, not less than 60%, preferably not less than 80%, further preferably not less than 90%, and particularly preferably not less than 95%. For example, homology between a base sequence represented by SEQ ID NO: 1 and a base sequence represented by SEQ ID NO: 2 is 79% (computed by GENETYX-MAC Ver.13; Genetyx Corporation). Nucleic acid sequence homology can be computed by commercial analysis tools, or by tools available through electric telecommunication lines (the Internet). Specifically, homology can be computed using BLAST analysis software (J. Mol. Biol., 215, 403-410, 1990). Nucleic acid sequence homologies can be searched using DNA sequence-related databases such as the DNA Database of Japan (DDBJ) (www.ddbj.nig.ac.jp/), Genebank (www.ncbi.nlm.nih.gov/web/Genebank/Index.htlm), the European Molecular Biology Laboratory Nucleic Acid Sequence Database (EMBL) (www.ebi.ac.uk/ebi docs/embl db.html), and the like.

Regarding the DNA of the above (b), the "activity of enhancing elongation of plant roots" of the protein encoded by the DNA can be confirmed as follows. A recombinant expression vector that contains a target DNA is used to prepare transgenic *Arabidopsis*. By self-pollination, T3 seeds of the transformed *Arabidopsis* are obtained. The T3 seeds are grown on a Murashige and Skoog medium that contains 2 wt. % sucrose under 100 μmol/m$^2$/s light illumination, with a photoperiod of 16 hours and a dark period of 8 hours, at 23° C. Two weeks later, the plants are measured for primary root length. Untransformed *Arabidopsis* is grown under the same conditions. Two weeks later, the plants are measured for primary root length. A protein encoded by a DNA is considered to have the "activity of enhancing elongation of plant roots" when the primary root length of the transgenic *Arabidopsis* is increased 1.1 times or greater, preferably 1.2 times or greater, more preferably 1.3 times or greater, further preferably 1.4 times or greater, particularly preferably 1.5 times or greater, as compared to the primary root length of the untransformed *Arabidopsis* grown under the same conditions.

Regarding the DNA of the above (b), the "activity of inhibiting elongation suppression in plant roots under hyperosmotic stress" of the protein encoded by the DNA can be confirmed as follows. Specifically, a recombinant expression vector that contains a target DNA is used to prepare transgenic *Arabidopsis*. By self-pollination, T3 seeds of the transformed *Arabidopsis* are obtained. The T3 seeds are grown on a ½-strength Murashige and Skoog medium under 100 μmol/m$^2$/s light illumination, with a 24-hour photoperiod at 23° C. for 3 days, and then transferred to a ½ strength Murashige and Skoog medium that contains 5 wt. % of polyethylene glycol 6,000. After growing under a 24-hour photoperiod at 23° C. for 4 days, the plants are measured for primary root length. At the same time, another cultivation is performed without polyethylene glycol using the same T3 seeds on a ½ strength Murashige and Skoog medium under the same conditions, and the plants are measured for primary root length. A protein encoded by a DNA is considered to have "activity of inhibiting elongation suppression in plant roots under hyperosmotic stress" when the primary root length of *Arabidopsis* grown on the polyethylene glycol-containing medium is increased by 0.85 times or greater, preferably 0.9 times or greater, further preferably 0.95 times or greater, as compared to the primary root length *Arabidopsis* grown on a polyethylene glycol-free medium.

Another aspect of the Ran gene of the present invention is a polynucleotide encoding a polypeptide of any of the following (c), (d) or (e):

(c) a polypeptide consisting of an amino acid sequence represented by SEQ ID NO: 3 or 4;

(d) a polypeptide that consists of an amino acid sequence represented by SEQ ID NO: 3 or 4, in which one or several amino acids are substituted, deleted, or added, and that has an activity of enhancing elongation of plant roots and an activity of inhibiting suppression of plant root elongation under hyperosmotic stress;

(e) a polypeptide that has homology of not less than 70% with the amino acid sequence represented by SEQ ID NO: 3 or 4, and that has an activity of enhancing elongation of plant roots and an activity of inhibiting suppression of plant root elongation under hyperosmotic stress.

The amino acid sequence represented by SEQ ID NO: 3 corresponds to the amino acid sequence that is encoded by the open reading frame (ORF) of the base sequence represented by SEQ ID NO: 1; the amino acid sequence represented by SEQ ID NO: 4 corresponds to the amino acid sequence encoded by the ORF of the base sequence represented by SEQ ID NO: 2.

In the peptide (d), the range of "one or several amino acids" is not particularly limited, and is specifically, for example, 1 to 40 amino acids, preferably 1 to 20 amino acids, more preferably 1 to 12 amino acids, further preferably 1 to 9 amino acids, and particularly preferably 1 to 5 amino acids.

Regarding the amino acid substitution in the peptide (d), it is more preferable to use similar amino acids because such a substitution is not expected to cause a phenotypic change; more specifically, such a substitution is considered a conservative amino acid substitution. Examples of the similar amino acid can be classified as follows. The conservative amino acid substitution is well known in this technical field (see Science, 247: 1306-1310 (1990)).

Aromatic amino acid: Phe, Trp, Tyr
Aliphatic amino acid: Ala, Leu, Ile, Va
Polar amino acid: Gln, Asn
Basic amino acid: Lys, Arg, H is
Acidic amino acid: Glu, Asp
Hydroxyl group-containing amino acid: Ser, Thr
Amino acid with small side chain: Gly, Ala, Ser, Thr, Met The technique for substituting, deleting, or adding one or several amino acids in a specific amino acid sequence is publicly known, and the production of a polynucleotide that encodes the polypeptide (d) is also carried out using a commercially available kit and the like, in accordance with a known method.

The polypeptide (e) preferably has homology of not less than 70%, more preferably not less than 90%, particularly preferably not less than 95% with the amino acid sequences of SEQ ID NOS: 3 or 4. For example, the homology between the amino acid sequences of SEQ ID NO: 3 and SEQ ID NO: 4 is 95% (computed by GENETYX-MAC Ver. 13, Genetyx Corporation). Herein, the "%" that represents amino acid sequence homology denotes a ratio (%) of degree of identity of two amino acid sequences; more specifically, a ratio (%) represents identity of amino acid sequences.

To securely provide the above desired activity to the polypeptide (e), the polypeptide preferably has a homology of not less than 80%, preferably not less than 85% with the amino acid sequence of SEQ ID NO: 3 in the region from 181st to 221st amino acids. The amino acid sequence homology between the amino acid sequences of SEQ ID NO: 3 and SEQ ID NO: 4 in this region is 88%.

Amino acid sequence homology can be computed by analysis tools that are available commercially or through electric telecommunication lines (the Internet). Specifically, homology can be computed by BLAST analysis software (J. Mol. Biol., 215, 403-410, 1990). The information about amino acid sequence homology can be found in databases regarding amino acid sequences of proteins, or in databases regarding predicted amino acid sequences based on DNA sequences, such as SWISS-PROT (http://www.ebi.ac.uk/swissprot/) or PIR (http://pir.georgetown.edu/).

The "activity of enhancing elongation of plant roots" and the "activity of inhibiting suppression of plant root elongation under hyperosmotic stress" required for the polypeptides (d) and (e) are confirmed by the same method as that for the DNA (b).

The Ran gene of the present invention can be obtained by the RT-PCR method. As a template, the total mRNA having been prepared from a wild watermelon derived-tissue according to a known method can be used. The primers are designed to amplify the full length of the Ran gene of the present invention. The Ran gene of the present invention can also be obtained by the PCR method using a wild watermelon-derived cDNA library as a template, with the primers designed to amplify the full length of the Ran gene of the present invention.

The PCR amplification of the Ran gene of the present invention is carried out in a reaction mixture containing a template polynucleotide, a PCR buffer, a primer set (a forward primer and a reverse primer), a dNTP mixture (a mixture of deoxyribonucleoside triphosphates) and a DNA polymerase, by repeating high and low temperature cycles. The forward primer and the reverse primer are designed, for example, based on about 10 to 50 bp nucleotide sequences at or in the vicinity of the 5' terminus and at or in the vicinity of the 3' terminus of the Ran gene of the present invention, and are synthesized according to a known method. When a sequence to be amplified does not contain a start codon, the forward primer is designed to contain a start codon in-frame, or a start codon is introduced in-frame into the expression vector described below. The PCR buffer is selected, for example, from commercially available products depending on the DNA polymerase to be used. The dNTP mixtures and the DNA polymerases can also be selected from commercially available products. The PCR reactions can be conducted according to a known procedure or the instruction for DNA polymerase. The reaction temperature, reaction time, reaction cycle, reaction composition and the like can be modified as needed.

The Ran gene of the present invention is introduced into a plant, and is expressed to exert an activity of enhancing root elongation. With this characteristic, the Ran gene of the present invention is useful as an agent for enhancing root elongation. Also, the Ran gene of the present invention is introduced into a plant, and is expressed to exert an activity of inhibiting the suppression of root elongation due to hyperosmotic stress, and therefore is useful as an agent for supporting plant root growth under hyperosmotic stress conditions.

Wild Watermelon-Derived Ran Protein

The polypeptide of the present invention corresponds to a Ran protein encoded by the Ran gene of the present invention, namely, the peptides of (c) to (e) above. The polypeptide of the present invention in a plant exerts an effect of enhancing root elongation in plants, and is therefore useful as an agent for enhancing root elongation. The polypeptide of the present invention in a plant also exerts an effect of inhibiting the suppression of root elongation due to hyperosmotic stress, and is therefore useful as an agent for supporting plant root growth under hyperosmotic stress. The expression of the polypeptide of the present invention in a plant is preferably brought about by a method of transforming a plant using a recombinant vector, which is prepared using the Ran gene of the present invention.

Recombinant Vector

The recombinant vector of the present invention can be prepared by inserting the Ran gene of the present invention into a plant cell transformation vector. The plant cell transformation vector is not particularly limited as long as it serves to introduce a gene into a plant cell. For example, Ti plasmid-derived pBI101, pBI121, pBI122 (Clontech Laboratories, Inc.), PBE2113-GUS (National Institute of Agrobiological Sciences), and the like may be used. As a direct transformation vector, pUC19 and the like may also be used. Plant virus-derived vectors such as geminivirus-derived virus vectors (WDV, and the like) and RNA virus-derived virus vectors (tobacco mosaic virus, cucumber mosaic virus, potyvirus-derived virus vectors, and the like) can also be used. Further, it is possible to directly introduce a functional DNA fragment cut out of a vector into a plant cell, or directly introduce a DNA fragment that does not have either or both of a promoter and poly A into the plant genome, using an endogenous promoter or a poly A signal for transcription control.

The Ran gene of the present invention may be inserted into a plant cell transformation vector by, for example, ligating the 5' terminus of a PCR-amplified Ran gene to a downstream portion of the 3' side of a promoter that functions in a plant, directly or through an appropriate sequence (for example, a restriction enzyme recognition site, or the like).

Further, a vector of the present invention may contain, aside from a promoter and the Ran gene of the present invention, a terminator, an enhancer, a selectable marker gene, and the like.

Preferable examples of usable selectable marker genes for a plant cell include, but are not particularly limited to, kanamycin phosphotransferase genes and hygromycin phosphotransferase genes, which confer antibiotic resistance; acetobutyric acid synthetic enzyme genes, which confer herbicide resistance; and dihydrofolate reductase genes, which confer methotrexate (MTX) resistance.

Plant Transformation Using the Ran Gene of the Present Invention

The recombinant vector of the present invention can be introduced into a target host plant to produce a transgenic plant having enhanced root elongation.

Usable forms of the host plant and the introduction sites include any of cultured plant cells; callus; protoplasts; whole plants of cultivated plants; plant tissues such as leaves, petals, stems, roots, root stems, seeds, and the like; and plant organs such as the epidermis, phloem, parenchyma, xylem, vascular bundle, and the like.

Examples of the host plants include monocots such as rice, wheat, barley, maize, *Sorghum*, coco, Araceae, Bromeliaceae, lilies, orchids, or ginger; and dicots such as tomatoes, beans, potatoes, sweet potatoes, sunflowers, tobacco, cucumbers, cabbage, lettuce, cassaya, willows, walnuts, beeches, roses, Camellia, Ericaceae, eggplants, sesame, Cucurbitaceae, or Chrysanthemum. Pteridophytes such as Equisetum, Selaginellaceae, Pteridium, Osmundaceae, and the like may also be used. Among these, rice, wheat, barley, corn, *Sorghum*, Araceae, tomatoes, beans, potatoes, sweet potatoes, sunflowers, eggplants, and Cucurbitaceae are preferable.

The Ran gene of the present invention is introduced into a host plant by a method using *Agrobacterium*, electroporation, particle gun method, microinjection and the like, among which the method using *Agrobacterium* is preferable.

The method using *Agrobacterium* is well known, and carried out by, for example, infecting a plant cell or a slice with the *Agrobacterium* having been introduced with the recombinant vector of the present invention (see Proc. Natl. Acad. Sci. USA., 94, 2117-2121, for example).

After the Ran gene of the present invention is introduced into a host plant, the plant cell having been introduced with the Ran gene of the present invention is selected to form a callus-like tissue. When the callus-like tissue puts out buds, the plant is transferred to a rooting medium to obtain a transgenic plant.

The selection of the plant cell introduced with the Ran gene of the present invention and the formation of the budded callus-like tissue are preferably carried out under the following culture condition. The Ran gene-introduced plant cell or the slice is cultured in an agar medium, such as Murashige and Skoog medium, that contains an appropriate amount of sucrose and the like, in the presence of an appropriate selectable agent according to the type of the introduced selectable marker gene, under a temperature of about 4 to 50° C., preferably about 15 to 37° C., further preferably about 22 to 30° C., for about 3 to 180 days, preferably about 7 to 90 days, and further preferably about 14 to 60 days. An optimum culture temperature can be found by carrying out an experimental culture for each plant. Some plants may require a longer culture period than the above-specified periods.

The resulting bud is transferred onto a known rooting medium such as a 4 µM indolebutyric acid containing Murashige and Skoog medium or the like, and cultured, for example, for about 3 to 180 days, preferably about 7 to 90 days, and further preferably about 14 to 60 days, into a plant. Then, the plant can be transferred into vermiculite or soil as needed to be grown therein. The transgenic plant of the present invention can also be assayed by Northern blot assay using DNA fragments of the Ran gene of the present invention as a probe, so as to find a transgenic plant strongly expressing the Ran gene of the present invention.

The transgenic plant having been introduced with the Ran gene can be tested to confirm that the Ran gene of the present invention is incorporated in the current and the next generations of the transgenic plant by detecting the Ran gene of the present invention from the genomic DNA of the cells or tissues by way of PCR, Southern blot analysis or the like.

The transgenic plant of the present invention thus prepared has enhanced root elongation, particularly for the primary root elongation. Such enhancement of plant root elongation provides the plants with useful improvements in growth, resistance against dry environments, enhancements in their ability to draw nutrients from soil, and the like. Hence, the application of the transgenic plant of the present invention to crops or tree plantation is very effective. Further, in the transgenic plant of the present invention, the root elongation is not suppressed even under hyperosmotic stress, therefore ensuring superior growth even under hyperosmotic stress. With this advantage, the transgenic plant of the present invention is very useful as crops or tree plantation in environments such as dry soil, hypersaline soil, or the like.

The transgenic plant of the present invention includes, but is not limited to, whole plants (whole arbores) including individual cells, callus thereof, seeds, plant tissues, leaves, stems, roots, flowers, fruits, and fibers. Further, their progenies and progeny plants of intraspecific or interspecific crosses are also included in the transgenic plant of the present invention.

A Method for Enhancing Plant Root Elongation

The present invention provides a method for enhancing plant root elongation, the method comprising introducing the Ran gene of the present invention into a plant and expressing the gene. Such introduction of the Ran gene of the present invention according to the present invention provides root elongation enhancement, particularly for primary root elongation, in the target plant. Such enhancement of root elongation improves the ability to draw nutrients and water from soil in the plant, thereby improving drought resistance in crops, increasing crop yield, and enhancing growth in tree plantation. Further, the root development strengthens the stability of the tree, and is useful for nourishing and maintaining windbreaks and environmental conservation.

A Method for Inhibiting the Suppression of Elongation in Plant Roots Under Hyperosmotic Stress The present invention provides a method for inhibiting suppression of plant root elongation under hyperosmotic stress, the method comprising introducing the Ran gene of the present invention into a plant and expressing the gene. The present invention can, by introducing the Ran gene of the present invention into a plant as above, inhibit the suppression of root elongation due to hyperosmotic stress. Such a method allows vigorous root elongation in dry soil, hypersaline soil, and the like, and is thereby preferably applied to plants that are exposed to hyperosmotic stress.

A Kit for Producing a Plant Having Enhanced Root Elongation, or A Plant Without Root Elongation Ability Suppressed, Even Under Hyperosmotic Stress A kit of the present invention is used to produce a plant having enhanced root elongation, or a plant immune to suppression of root elongation even under hyperosmotic stress. The kit containing a recombinant vector of the present invention may include a reagent, an instruction and the like as needed, to introduce the recombinant vector into a plant cell.

EXAMPLES

The present invention is more specifically explained with reference to the Examples below, but is not limited by such examples.

Reference Example 1

Analysis of the Influence of Drought Stress to the Expression of the Protein Derived from Wild Watermelon Root Wild watermelon was exposed to drought stress, and the type and amounts of proteins expressed before and after the drought stress in the root were analyzed to detect and identify the growth related proteins under drought stress. Specifically, experiments were carried out as follows.

1. Cultivation of Wild Watermelon

Wild watermelon seeds, native to the Republic of Botswana's Kalahari Desert (*Citrullus lanatus* sp. No. 101117-1: preserved at Tottori Prefectural Horticultural Exp. Stn.), were soaked in distilled water and incubated at 37° C. for about 20 hours. Artificial soil Isolite (particle size: 2 mm, Isolite Insulating Products Co., Ltd.) was placed into a paper pot (750 ml), and the soaked seeds were sown and grown in a phytotron (light period: temperature 35° C., humidity 50%, light intensity 700 mmol photons $m^{-2}$ $s^{-1}$, 16 hours; dark period: temperature 25° C., humidity 60%, 8 hours) (strong light conditions) until their fourth leaf completely expanded (for about 20 days), with daily watering (about 125 ml/pot). A 2,000-fold diluted liquid fertilizer (HYPONeX; N:P:K=6:10:5; product of HYPONeX Japan Corp., Ltd.) was used for watering. After the fourth leaf completely expanded, drought stress was imposed by withholding watering, and the roots were harvested after 0, 1, and 3 days.

2. Extraction of Soluble Proteins from Wild Watermelon Roots

Drought-stressed wild watermelon roots at day 0, day 1, and day 3 (3 or 4 roots each, about 2.5 g), preserved at −80° C., were ground to powder in a liquid nitrogen-containing mortar. After adding about 50 ml of a homogenizing buffer (61.5 mM $K_2HPO_4$, 38.5 mM $KH_2PO_4$, pH 7.0, 2 mM $MgCl_2$, 10 mM NaCl, 1 mM EDTA, 10 mM β-ME, 1 mM PMSF), the ground roots were ground further, and filtered through 4 layers of gauze (Suzuran Sanitary Goods Co., Ltd.). The resulting extract was dispensed into 50 ml centrifuge tubes, and centrifuged (2,000×g, 4° C., 10 seconds) to eliminate contaminants, unhomogenized cells, and the like. The supernatant was transferred to fresh 50 ml centrifuge tubes, and ultracentrifuged (100,000×g, 4° C., 1 hour). Subsequently, the supernatant (soluble fraction) was transferred to fresh 50 ml tubes, an equal amount of TCA was added, and the resulting solution was allowed to stand on ice for 30 minutes. After centrifuging the solution (15,000×g, 4° C., 15 minutes) and removing the supernatant, the precipitate was suspended in 100% acetone and centrifuged (15,000×g, 4° C., 15 minutes), and then the supernatant was removed to obtain an acetone precipitate.

3. Fractionation of Soluble Proteins by Two-Dimensional Electrophoresis 3-1. Sample Preparation The above-obtained acetone precipitate was dissolved in a 2-DE buffer (7 M urea, 2 M thiourea, 4 wt. % CHAPS, 0.5% (v/v) Triton X-100, 0.5% (v/v) Immobiline pH Gradient buffer: pH 4-7 (Amersham Pharmacia Science), 100 mM DTT). After stirring at room temperature for 30 minutes, the solution was centrifuged (15,000×g, 4° C., 1 hour, room temperature) to obtain the supernatant as a two-dimensional electrophoresis sample. The sample was dispensed and stored at −80° C. Proteins dissolved in the 2-DE buffer were quantitated using a 2-D Quant Kit (Amersham Pharmacia Science).

3-2. Gel Rehydration

A rehydration tray for 24-cm DryStrip gel (Amersham Pharmacia Science) was placed horizontally, and 450 µl of a rehydration solution (the same composition as for the 2-DE buffer) containing the protein sample was loaded per lane. When using a rehydration tray for 11-cm DryStrip gel, 240 µl of the rehydration solution was loaded per lane in the same manner. After removing the film from Immobiline DryStrips: 24 cm, pH 4-7 (Amersham Pharmacia Science), the strips were placed in the tray with the gel surface facing down, in a manner to avoid trapping air, and covered with 1.5 to 3 ml of silicone oil: KF-96-1.5CS (Shin-Etsu Chemical Co., Ltd.) per lane to prevent water evaporation and urea precipitation. Subsequently, the strips were allowed to stand for 14 to 20 hours (at 4° C.) for gel rehydration.

3-3. Immobilized pH Gradient Isoelectric Focusing (IEF)

The first dimension electrophoresis was carried out using Multiphor™II (Amersham Pharmacia Science). The rehydrated strip gels were placed on the electrophoresis layer, and the electrophoresis tray was filled with silicone oil to prevent the gel from drying. The electrophoresis conditions were as follows. Step 1: 500 V gradient, 2 mA, 5 W, 1 min, 15° C.; step 2: 500 V, 2 mA, 5 W, 4 hrs, 15° C.; step 3: 3,500 V gradient, 2 mA, 5 W, 8 hrs, 15° C.; and step 4: 3,500 V, 2 mA, 5 W, 40 hrs or more.

3-4. Equilibration

After completing the isoelectric point electrophoresis, the strip gels were shaken for 15 minutes at room temperature in 10 ml of a first equilibration buffer (50 mM Tris-HCl (pH 8.8), 6M urea, 30% (w/v) glycerol, 2% (v/v) SDS, 65 mM DTT) per strip gel. After removing the first equilibration buffer, 10 ml of a second equilibration buffer (50 mM Tris-HCl (pH 8.8), 6 M urea, 30% (w/v) glycerol, 2% (v/v) SDS, 135 mM iodoacetamide) was added, and the strip gels were shaded with aluminium foil and shaken at room temperature for 15 minutes. After equilibration, an electrode buffer (25 mM Tris-HCl (pH 8.8), 190 mM glycine, 3.5 mM SDS) was added to the strip gels to wash away the equilibration buffer.

3-5. SDS-PAGE

The second dimension electrophoresis was carried out using an Ettan DALTsix Electrophoresis System (Amersham Pharmacia Science). An acrylamide gel solution (final concentrations: 30% acrylamide, 0.8% N,N,-methylenebisacrylamide, 1.5M Tris-HCl (pH 8.8), 10% SDS, 10% APS, 10% TEMED was poured into a cassette placed into an Ettan DALTsix Gel Caster, and adjusted to make the gel surface even by adding an adequate amount of water-saturated butanol onto the gel. The gel was allowed to stand for at least 20 hours at 4° C. to allow complete polymerization.

The equilibrated strip gels were placed onto the gel prepared. An embedding agarose gel (an electrode buffer containing 0.5% agarose and an adequate amount of Bromophenol Blue) was melted at 100° C. and cooled to around 70° C., and poured to fix the strip gels. Subsequently, the lower buffer chamber of Ettan DALTsix was filled with a 1× electrode buffer (about 4 L), and the inside of the chamber was pre-cooled to 10° C. using a thermostatic circulator. After placing the gel with the strip gels in the lower chamber, the upper buffer chamber was inserted over the lower buffer chamber, and filled with a 2× electrode buffer (about 800 ml) to reach the level of the buffer in the lower chamber. Electrophoresis was carried out using Multiphor™II (Amersham Pharmacia Science), under the conditions of step 1: 600 V, 400 mA, 2.5 W/gel, 30 mins; and step 2: 600 V, 400 mA, 100 W, 3.5 to 5 hrs.

3-6. Gel Staining

The gel was stained using a Colloidal Blue Staining Kit (Invitrogen Corporation). A 100 ml quantity of a staining solution was used per one sheet of the gel. The gel was stained and destained at room temperature for not less than 40 hours, and then shaken in ultrapure water for not less than 24 hours.

3-7. Quantitative Determination of Protein Spots Using HT Analyzer

Figure 1:
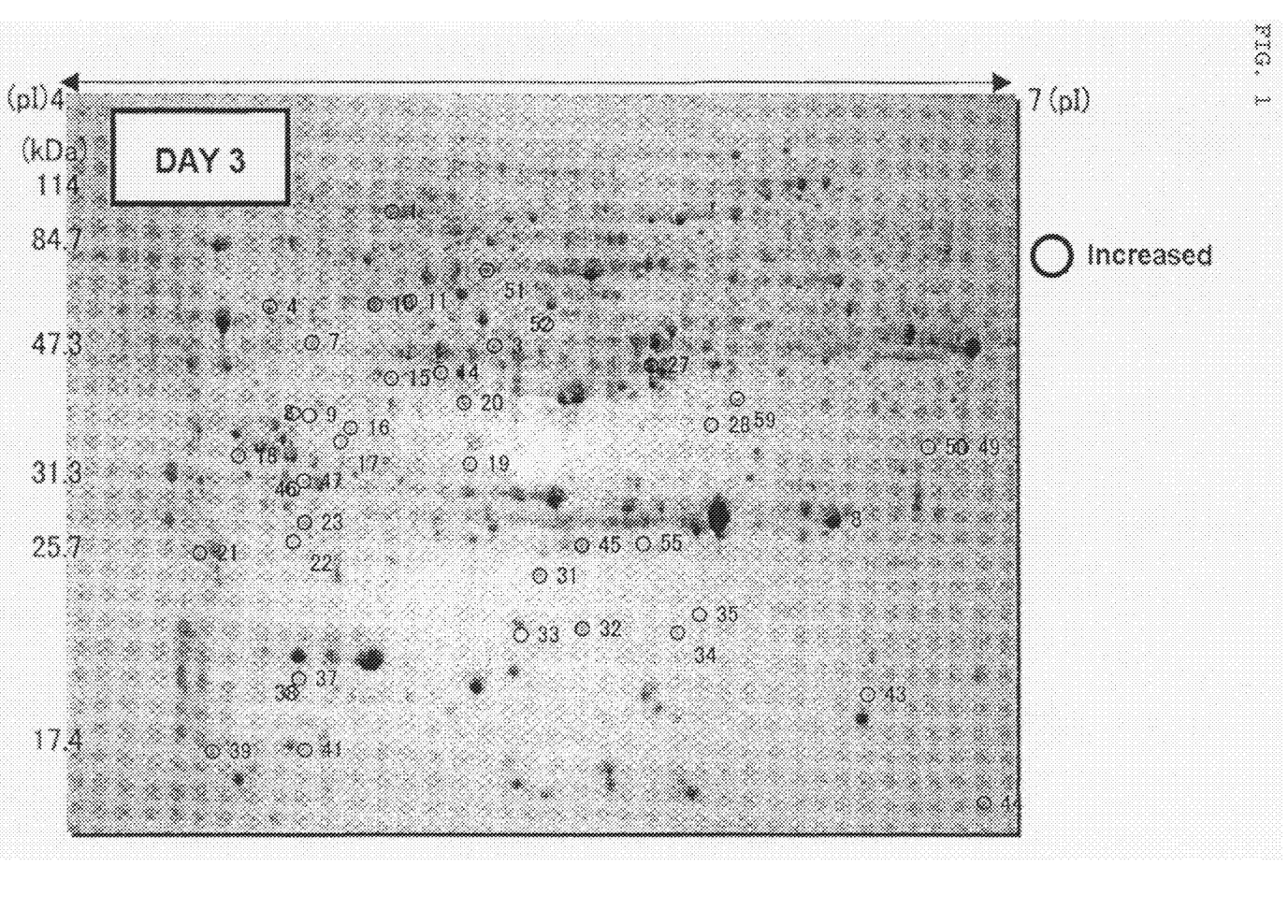
FIG. 1 shows the data of Reference Example 1; a two-dimensional electrophoretogram of proteins expressed in the roots of wild watermelon after a three-day drought stress. In the figure, the circled areas indicate protein spots displaying enhanced intensity as a result of the drought stress.

The entire gel image was photographed using ProPic (Genomic Solutions), and protein spots were detected and quantitatively analyzed using an HT Analyzer (Genomic Solutions). To avoid misrecognition of spots, two-dimensional electrophoretic profiles on day 0, day 1 and day 3 of drought stress were visually compared and corrected, to detect protein spots where the intensity increased with time after the drought stress, using an HT Analyzer. FIG. 1 indicates the two-dimensional electrophoretic profile of proteins expressed in the wild watermelon roots on day 3 of the drought stress. For quantitative determination of the spot intensity, fluctuations in the protein amounts or staining intensity among gels were corrected using about 10 selected spots without intensity change. The background around each spot was automatically corrected using the HT Analyzer.

3-8. Peptide Fragmentation of Proteins by In-Gel Digestion

Each of the multiple protein spots showing increased intensity after imposition of drought stress was excised, and transferred into a TPX centrifuge tube. After dehydrating the gel by adding 100 µl of acetonitrile and shaking the tube for 15 minutes, the gel was completely dried using a centrifugal evaporator (30 minutes). A 40 µl quantity of 10 mM DTT/100 mM $NH_4HCO_3$ was added, and incubation was carried out for 45 minutes at 56° C. to reduce the disulfide bond of each protein to an SH group. To avoid reoxidation of the SH group, after removing the solution, 40 µl of 55 mM iodoacetamide ($ICH_2CONH_2$)/100 mM $NH_4HCO_3$ was added, and incubated at room temperature in the dark for 30 minutes for alkylation. After dehydrating the gel with acetonitrile, the gel was dried using a centrifugal evaporator, 40 µl of 12.5 ng/µl trypsin (MS grade, Promega Corporation)/50 mM NH$_4$HCO$_3$ was added, followed by incubation at 4° C. for 45 minutes. Subsequently, the solution was removed, the gel pieces were washed with 100 μl of 50 mM NH$_4$HCO$_3$, 20 μl of 50 mM NH$_4$HCO$_3$ was added again, and the mixture was allowed to react at 37° C. for 16 hours for trypsin digestion. After digestion with trypsin, the solution was transferred to a fresh TPX centrifuge tube. A 10 μl quantity of 25 mM NH$_4$HCO$_3$ was added to the gel pieces, and shaken for 10 minutes. A 20 μl quantity of acetonitrile was added and further shaken for 10 minutes. The resulting mixture was transferred to a TPX centrifuge tube. A 10 μl quantity of 5% formic acid (Wako) was added to the gel pieces, and shaken for 10 minutes. A 25 μl quantity of acetonitrile was added, further shaken for 10 minutes, and then transferred to a TPX centrifuge tube. This process was repeated twice. Because complete drying makes resuspension difficult, the solution in a collection centrifuge tube was evaporated to about 20 μl using a centrifugal evaporator, and finally 5 μl of formic acid was added.

3-9. Protein Identification by Ion Trap Liquid Chromatography-Tandem Mass Spectrometry (LC-MS/MS)

The above trypsin-digested peptide fragments were analyzed by ion trap liquid chromatography-tandem mass spectrometry (LC-MS/MS: LCQ-Advantage Thermo Electron Corporation). The mass spectrometry data obtained was subjected to a homology search targeting plants, in the non-redundant database of the NCBI (National Center of Biotechnological Information) database using MSCOT (Matrix Science Ltd.).

As a result, a Ran protein (CLRAN1: SEQ ID NO: 1; CLRAN2: SEQ ID NO: 2) was detected and identified as a protein that was expressed in a remarkably increased amount in the roots after imposition of drought stress. Based on this result, the following experiments were carried out, focusing attention on the wild watermelon-derived Ran gene.

Example 1 cDNA Cloning of Wild Watermelon-Derived Ran Gene CLRAN1 (DRIP-49)

From wild watermelon roots (*Citrullus lanatus* sp. No. 101117-1: preserved at Tottori Prefectural Horticultural Exp. Stn.), native to the Republic of Botswana's Kalahari Desert, the total RNA was extracted using TRIzol (Invitrogen Corporation). From 5 μg of the total RNA obtained, 1st strand cDNA was prepared using an Oligo (dT) primer, and a target cDNA was amplified by RT-PCR using primers: CLRAN1FL-F:5'-gataccttcctctcgctttt-3' (SEQ ID NO: 5); and CLRAN1FL-R:5'-gcaaagagcatcatcaccac-3' (SEQ ID NO: 6). RT-PCR was carried out using ReverTra -Plus-™ Kit (Toyobo Co., Ltd.) according to the protocol attached to the kit. Specifically, 5 μl of the Oligo (dT) primer was added to 1 μg of the total RNA, a reaction mixture adjusted in total amount to 12 μl was processed at 65° C. for 5 minutes, and then quenched in ice. 4 μl of 5×RT buffer, 2 μl of 10 mM dNTPs, 1 μl of RNase Inhibitor, 1 μl of ReverTra Ace were added thereto to adjust the total amount to 20 μl, followed by processing at 42° C. for 60 minutes and then at 85° C. for 5 minutes. To 2 μl of this reaction product, 5 μl of 10×PCR buffer, 1 μl of KOD-Plus-, 3 μl of 25 mM MgSO$_4$, 1 μl of 10 mM dNTPs, and 15 pmol each of CLRAN1FL-F and CLRAN1FL-R were added, adjusted to 50 μl in total. The mixture was treated at 94° C. for 2 minutes, and then subjected to a repeated cycle of 98° C. for 10 seconds, 55° C. for 30 seconds, and 68° C. for 1 minute, 30 times, to obtain cDNA. The resulting amplified cDNA fragments were subjected to 1% agarose electrophoresis, followed by purification using a QIAquickGel Extraction Kit (Qiagen, Inc.), and cloned into pT7Blue-2 T-Vector (Novagen, Inc.) using a DNA Ligation Kit (TaKaRa Inc.). The DNA sequence was determined using a BigDye Terminator Cycle Sequencing Kit (Applied Biosystems, Inc.), with an ABI PRISMTM310 Genetic Analyzer (Applied Biosystems, Inc.). The result confirmed that the wild watermelon-derived Ran gene CLRAN1 (DRIP-49) (total length 666 bps, a polynucleotide represented by SEQ ID NO: 1) was successfully cloned.

Example 2

Construction of Plasmid to be Introduced

Based on the full-length cDNA of CLRAN1 (DRIP-49) obtained in Example 1, 666 bps of full length ORF was amplified by PCR using primers: CLRAN1-F: 5'-aaaaagcag-gctccttttccaatggctt-3' (SEQ ID NO: 7); and CLRAN1-R:5'-agaaagctgggtttttactcgaacgcg-3' (SEQ ID NO: 8). This ORF was introduced into a plant cell transformation vector, pGWB2, between cauliflower mosaic virus 35S promoter and nopaline synthase terminator, by way of recombinant reaction using a GATEWAY system (Invitrogen Corporation) to construct a CLRAN1 (DRIP-49) plasmid.

Example 3

Preparation of Ran Gene CLRAN1 (DRIP-49) Introduced Recombinant *Arabidopsis*

The CLRAN1 (DRIP-49) plasmid was used to transform *Agrobacterium tumefaciens* EHA105 strain by electroporation. *Arabidopsis* transformation was carried out according to a known method, by vacuum infiltration using *Agrobacterium* (Cell engineering additional volume, Plant cell engineering series 21, revised 3rd ed., Experimental Protocol in Model Plant: rice, *Arabidopsis*, and bird's-foot trefoil, Chapter 4, paragraph 4, "Transformation of *Arabidopsis* by vacuum infiltration and floral dipping", 3rd ed. first copy, Shujunsha (Apr. 5, 2005)).

Next, *Agrobacterium*-infected *Arabidopsis* (T0 generation) was grown in a Murashige and Skoog medium containing hygromycin (100 mg/l), kanamycin (50 mg/l), and sucrose (20 g/l), under 50 micro/mol/m2/s light illumination and 24-hour photoperiod at a temperature of 23° C. to carry out selection. The selected plants were transferred to soil (Metro-Mix® 350; product of Sun Gro Horticulture Inc.), further cultivated under the same conditions, and then T1 seeds were collected. After confirming the expression of transgenic gene-derived CLRAN1 (DRIP-49) mRNA by Northern blotting, T1 plants were further self-pollinated to obtain T3 seeds.

Experimental Example 1

Evaluation of Recombinant *Arabidopsis* for Root Elongation

Six lines of T3 seeds (RAN1-2, RAN1-3, RAN1-4, RAN1-6, RAN1-7, and RAN1-9) obtained in Example 3 were grown in a Murashige and Skoog medium agar medium containing 2 wt. % of sucrose, under 100 μmol/m$^2$/s light illumination, a 16-hour photoperiod and an 8-hour dark period at 23° C. for 2 weeks. Thereafter, the primary root lengths of the plants were measured. As a control, T3 seeds of *Arabidopsis* that was transformed with pGWB2 vector without the insert were grown in the same manner, and the primary root lengths of the plants obtained were measured.

Figure 2:
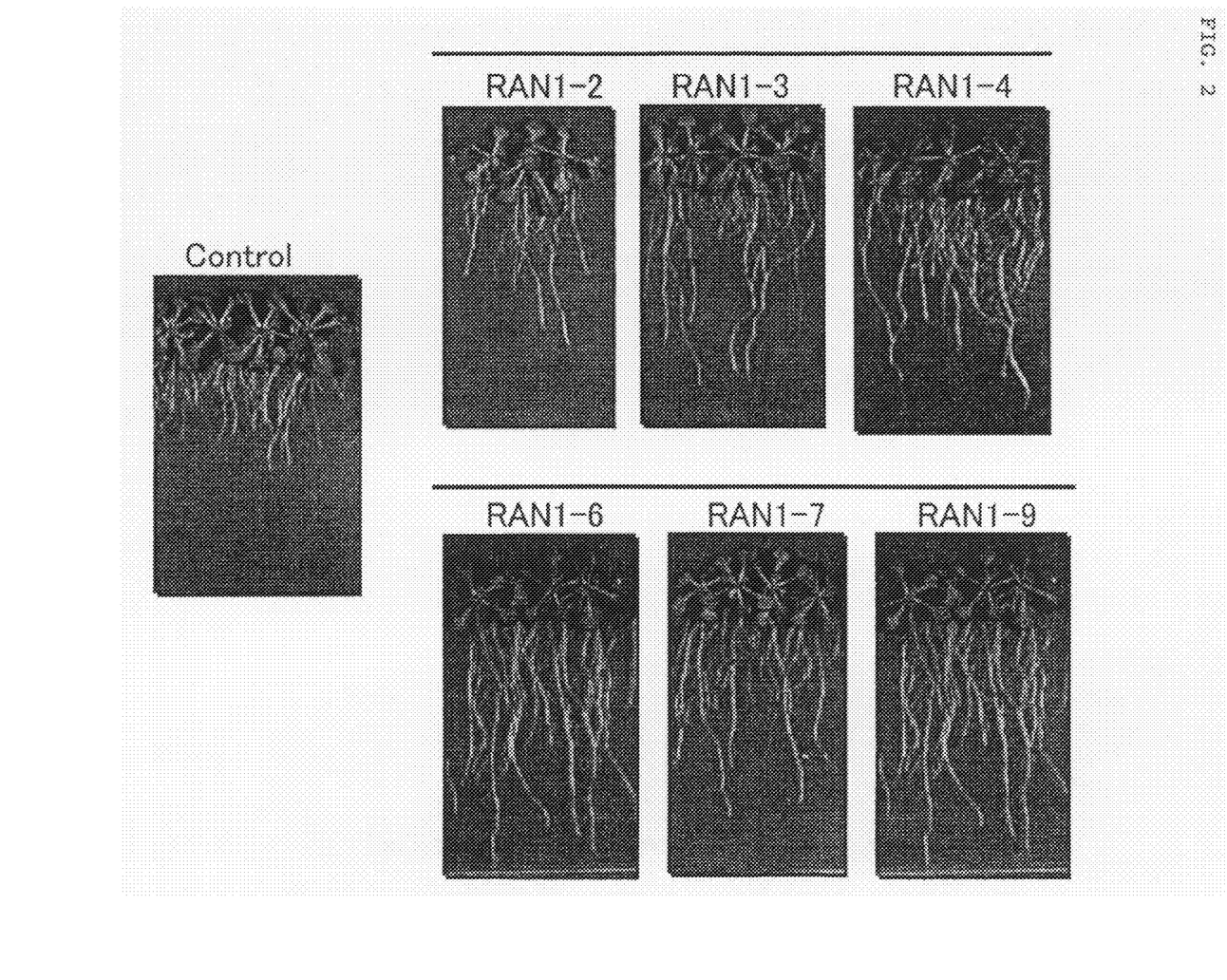
FIG. 2 shows the examination results of Experimental Example 1; images of root conditions in the growth of the recombinant *Arabidopsis* obtained in Example 3.
Figure 3:
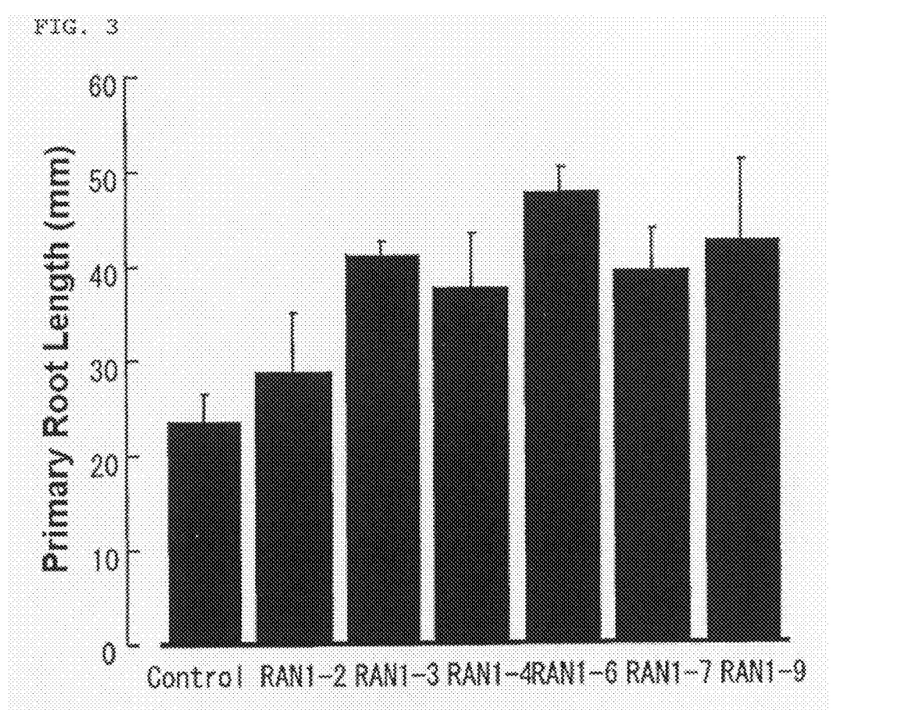
FIG. 3 shows the examination results of Experimental Example 1; a graph of primary root lengths in the growth of the recombinant *Arabidopsis* obtained in Example 3.

FIGS. 2 and 3 show the results. These results confirmed that the wild watermelon-derived Ran gene expressing recombinant *Arabidopsis* demonstrated primary root elongation enhancement.

Experimental Example 2

Evaluation of Recombinant *Arabidopsis* for Root Elongation under Hyperosmotic Stress Two lines of T3 seeds (RAN1-6 and RAN1-11) obtained in Example 3 were grown in a ½ strength Murashige and Skoog medium without sucrose under the conditions of 100 μmol/m$^2$/s light illumination and 24-hour photoperiod at a temperature of 23° C. for 3 days. Thereafter, seedlings were transferred to a 5 wt. % polyethylene glycol 6,000-containing ½ strength Murashige and Skoog medium, grown at 23° C. for 4 days, and the primary root length was measured. T3 seeds of *Arabidopsis* transformed with pGWB2 vector without the insert were used as a control.

Figure 4:
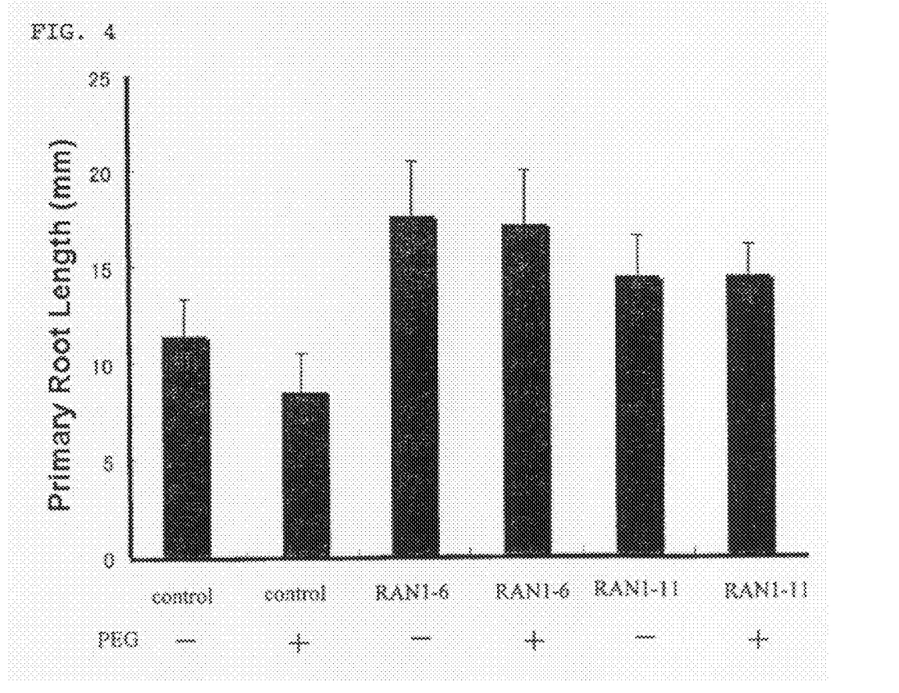

FIG. 4 shows the results. The control line demonstrated significant inhibition of primary root elongation that is caused by osmotic stress induced by the addition of 5 wt. % polyethylene glycol 6,000. In contrast, the effect of the osmotic stress was not seen in the two lines of recombinant *Arabidopsis* obtained in Example 3.

The invention claimed is:

1. An isolated polynucleotide consisting of the DNA of the base sequence of SEQ ID NO:1.

2. An isolated polynucleotide encoding a polypeptide consisting of the amino acid sequence of SEQ ID NO: 3.

3. A recombinant vector comprising the polynucleotide of claim 1.

4. A transgenic plant transformed with the polynucleotide of claim 1.

5. A method for producing a plant having enhanced root elongation, comprising a step of transforming a plant with an isolated polynucleotide, wherein the isolated polynucleotide encodes a polypeptide selected from the group consisting of:

(a) a polypeptide consisting of the amino acid sequence of SEQ ID NO:3;

(b) a polypeptide that consists of the amino acid sequence of SEQ ID NO:3 in which 1 to 12 amino acids are substituted, deleted, or added, and that has an activity of enhancing elongation of plant roots and an activity of inhibiting suppression of plant root elongation under hyperosmotic stress.

6. A method for producing a plant immune to suppression of root elongation under hyperosmotic stress, comprising a step of introducing an isolated polynucleotide into a plant cell, wherein the isolated polynucleotide encodes a polypeptide selected from the group consisting of:

(a) a polypeptide consisting of the amino acid sequence of SEQ ID NO:3;

(b) a polypeptide that consists of the amino acid sequence of SEQ ID NO:3 in which 1 to 12 amino acids are substituted, deleted, or added, and that has an activity of enhancing elongation of plant roots and an activity of inhibiting suppression of plant root elongation under hyperosmotic stress and regenerating a plant from said plant cell.

7. A method for enhancing plant root elongation, comprising a step of introducing an isolated polynucleotide into a plant cell, wherein the isolated polynucleotide encodes a polypeptide selected from the group consisting of:

(a) a polypeptide consisting of the amino acid sequence of SEQ ID NO:3;

(b) a polypeptide that consists of the amino acid sequence of SEQ ID NO:3 in which 1 to 12 amino acids are substituted, deleted, or added, and that has an activity of enhancing elongation of plant roots and an activity of inhibiting suppression of plant root elongation under hyperosmotic stress and regenerating a plant from said plant cell.

8. An agent for enhancing plant root elongation, comprising the polynucleotide of claim 1.

9. A method for inhibiting suppression of plant root elongation under hyperosmotic stress, comprising a step of introducing an isolated polynucleotide into a plant, wherein the isolated polynucleotide encodes a polypeptide selected from the group consisting of:

(a) a polypeptide consisting of the amino acid sequence of SEQ ID NO:3;

(b) a polypeptide that consists of the amino acid sequence of SEQ ID NO:3 in which 1 to 12 amino acids are substituted, deleted, or added, and that has an activity of enhancing elongation of plant roots and an activity of inhibiting suppression of plant root elongation under hyperosmotic stress.

10. A kit for producing a plant having enhanced root elongation, or for producing a plant immune to suppression of root elongation under hyperosmotic stress, said kit comprising the recombinant vector of claim 3.

* * * * *